United States Patent
Ozaki et al.

(10) Patent No.: US 10,180,387 B2
(45) Date of Patent: Jan. 15, 2019

(54) IDENTIFICATION DEVICE AND IDENTIFICATION METHOD

(71) Applicants: NATIONAL UNIVERSITY CORPORATION HAMAMATSU UNIVERSITY SCHOOL OF MEDICINE, Hamamatsu-shi, Shizuoka (JP); HAMAMATSU PHOTONICS K.K., Hamamatsu-shi, Shizuoka (JP)

(72) Inventors: Yusuke Ozaki, Hamamatsu (JP); Hidenao Iwai, Hamamatsu (JP); Hiroyuki Konno, Hamamatsu (JP); Hirotoshi Kikuchi, Hamamatsu (JP); Toyohiko Yamauchi, Hamamatsu (JP)

(73) Assignees: NATIONAL UNIVERSITY CORPORATION HAMAMATSU UNIVERSITY SCHOOL OF MEDICINE, Hamamatsu-shi, Shizuoka (JP); HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 53 days.

(21) Appl. No.: 15/329,456

(22) PCT Filed: Jul. 23, 2015

(86) PCT No.: PCT/JP2015/071023
§ 371 (c)(1),
(2) Date: Jan. 26, 2017

(87) PCT Pub. No.: WO2016/017533
PCT Pub. Date: Feb. 4, 2016

(65) Prior Publication Data
US 2017/0212033 A1 Jul. 27, 2017

(30) Foreign Application Priority Data
Jul. 29, 2014 (JP) .................................. 2014-153651

(51) Int. Cl.
*G06K 9/00* (2006.01)
*G01N 15/14* (2006.01)
(Continued)

(52) U.S. Cl.
CPC ......... *G01N 15/1429* (2013.01); *G01B 11/06* (2013.01); *G01N 15/0227* (2013.01);
(Continued)

(58) Field of Classification Search
CPC ........... G01N 15/1429; G01N 15/1459; G01N 15/1463; G01N 15/147; G01N 15/1434;
(Continued)

(56) References Cited

U.S. PATENT DOCUMENTS 8,538,119 B2 * 9/2013 Taki .................. G01N 15/1463
382/133
2008/0317325 A1 * 12/2008 Ortyn .................. G01N 15/147
382/133
(Continued)

FOREIGN PATENT DOCUMENTS

JP 2009-210542 A 9/2009
JP 2010-203949 A 9/2010
(Continued)

OTHER PUBLICATIONS

International Preliminary Report on Patentability dated Feb. 9, 2017 for PCT/JP2015/071023.

*Primary Examiner* — Jose L Couso
(74) *Attorney, Agent, or Firm* — Drinker Biddle & Reath LLP

(57) ABSTRACT

The identification apparatus includes a quantitative phase image acquisition unit, a feature quantity extraction unit, a learning unit, a storage unit, and an identification unit. The feature quantity extraction unit extracts a feature quantity of a quantitative phase image of a cell. The learning unit
(Continued)

performs machine learning for a quantitative phase image of a known cell of which a type is known based on the feature quantity extracted by the extraction unit. The storage unit stores a result of the machine learning by the learning unit. The identification unit determines, based on the feature quantity extracted by the extraction unit for the quantitative phase image of an unknown cell of which a type is unknown, the type of the unknown cell using the learning result stored by the storage unit.

10 Claims, 13 Drawing Sheets

(51) Int. Cl.
  *G01B 11/06* (2006.01)
  *G01N 15/02* (2006.01)
  *G01N 15/10* (2006.01)
  *G06T 7/00* (2017.01)
  *G01N 15/00* (2006.01)

(52) U.S. Cl.
  CPC ............ *G01N 15/10* (2013.01); *G01N 15/14* (2013.01); *G01N 15/1463* (2013.01); *G01N 15/1475* (2013.01); *G06K 9/00147* (2013.01); *G06T 7/0014* (2013.01); *G01N 2015/008* (2013.01); *G01N 2015/025* (2013.01); *G01N 2015/1018* (2013.01); *G01N 2015/1493* (2013.01); *G06T 2207/30024* (2013.01)

(58) Field of Classification Search
  CPC ............ G01N 15/14; G01N 15/1475; G01N 15/1404; G01N 15/00; G01N 15/10; G01N 21/17; G01N 21/27; G01N 21/45; G01N 33/4915; G01N 33/49; G01N 33/5094; G01N 2015/1493; G01N 2015/1409; G01N 2015/1006; G01N 2015/145; G01N 2015/149; G01N 2015/008; G01N 2015/0065; G01N 2015/1087; G01B 11/06; G01B 11/0675; G01B 9/02032; G01B 9/02047; G01B 9/02064; G01B 9/0207; G01B 9/02084; G01B 9/02091; G01B 9/04; G02B 27/1086; G02B 27/50; G02B 21/14; G02B 21/002; G02B 21/365; G02B 21/0056; G02B 21/244; G03H 1/0443; G03H 2001/005; G03H 2001/0456; G03H 2222/24; G06T 2207/30024; G06T 2207/30004; G06T 2207/10056; G06T 2207/10061; G06T 2207/30072; G06T 7/0012; G06T 7/62; G06T 2210/41; G06K 9/00127; G06K 9/00496; G06K 9/6289; G06K 9/0014; G06K 9/00147; G06K 2209/403; G06K 2209/05; G06K 2017/009; C12M 1/34; Y10S 977/869; Y10S 977/881; Y10S 977/904; Y10S 128/92; Y10S 706/924; Y10S 706/92
  See application file for complete search history.

(56) References Cited

U.S. PATENT DOCUMENTS

| | | | |
|---|---|---|---|
| 2009/0006003 A1* | 1/2009 | Hirayama | G01N 15/1012 702/21 |
| 2010/0284016 A1 | 11/2010 | Teitell et al. | |
| 2010/0290041 A1* | 11/2010 | Graham | C03B 23/04 356/246 |
| 2013/0130307 A1 | 5/2013 | Sugiyama et al. | |
| 2013/0229663 A1* | 9/2013 | Yang | A61B 5/0062 356/497 |
| 2013/0314526 A1* | 11/2013 | Yasuda | G01N 15/1475 348/79 |
| 2014/0178865 A1* | 6/2014 | Reed | G01B 11/0675 435/6.1 |
| 2014/0193892 A1 | 7/2014 | Mohan et al. | |
| 2014/0273067 A1* | 9/2014 | Wanders | G01N 33/5094 435/29 |
| 2015/0204728 A1* | 7/2015 | Liu | G01J 9/02 356/497 |
| 2015/0247802 A1* | 9/2015 | Ozasa | G01N 15/1429 435/6.15 |
| 2016/0061711 A1* | 3/2016 | Deka | G01N 33/5094 435/7.24 |
| 2016/0252447 A1* | 9/2016 | Kotz | G01N 15/1436 435/288.7 |
| 2016/0370280 A1* | 12/2016 | Yamamoto | G01N 15/1427 |

FOREIGN PATENT DOCUMENTS

| | | |
|---|---|---|
| JP | 2014-039535 A | 3/2014 |
| JP | 2014-508922 A | 4/2014 |
| JP | 5470625 B2 | 4/2014 |
| WO | WO 2005/029413 | 3/2005 |
| WO | WO-2009/147931 A1 | 12/2009 |
| WO | WO-2012/103233 A1 | 8/2012 |
| WO | WO 2013/019984 | 2/2013 |

* cited by examiner

*Fig.3*
(a)
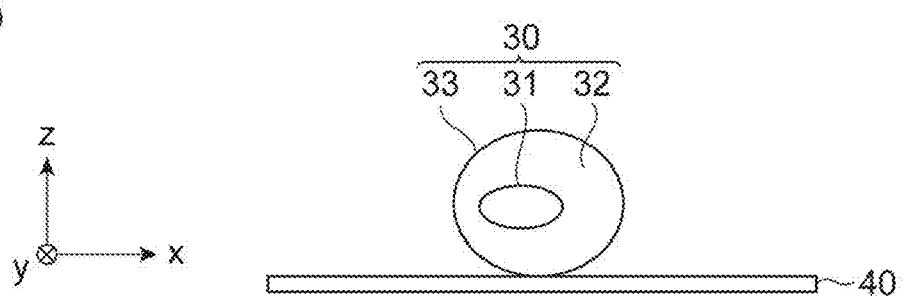
(b)
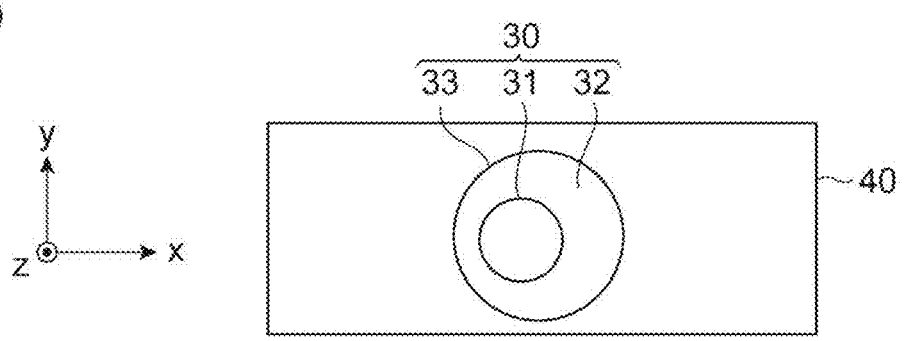

*Fig.4*
(a)
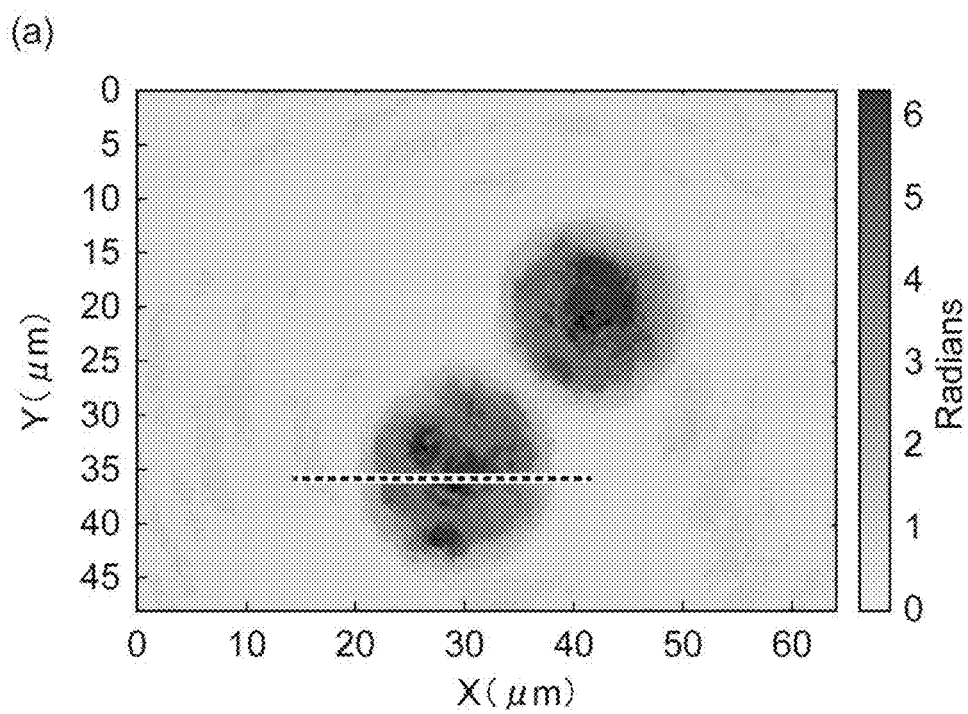
(b)
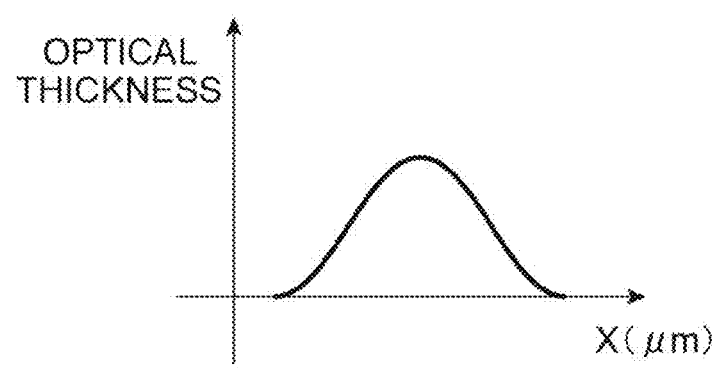

*Fig.5*
(a)
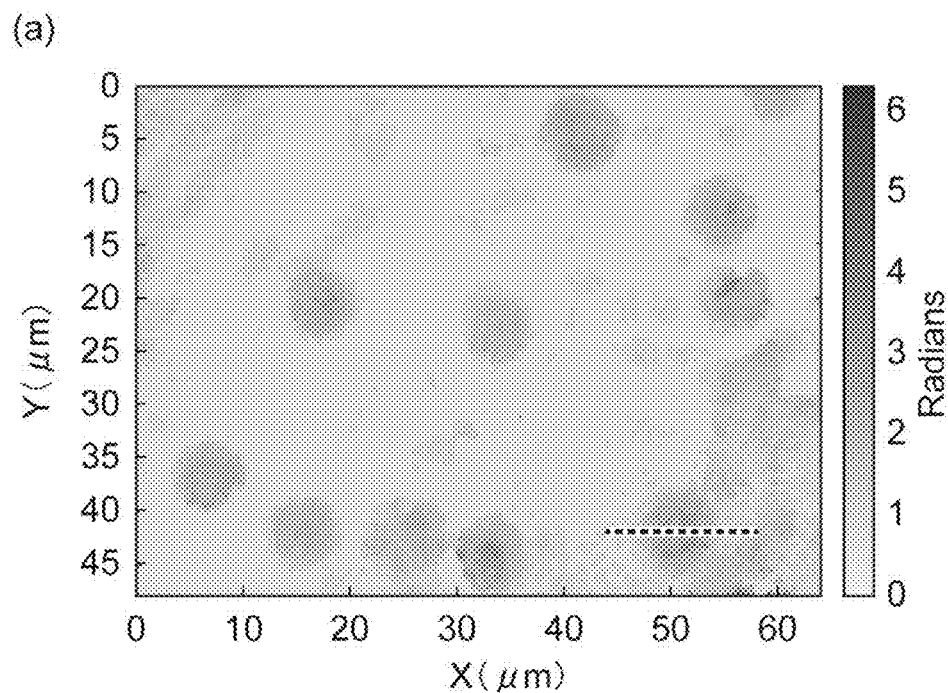
(b)
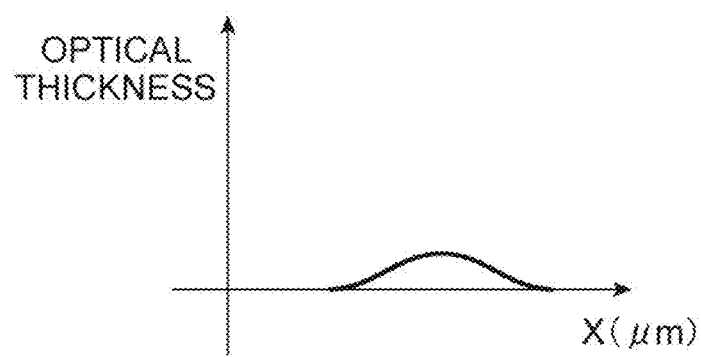

*Fig.11*
(a)
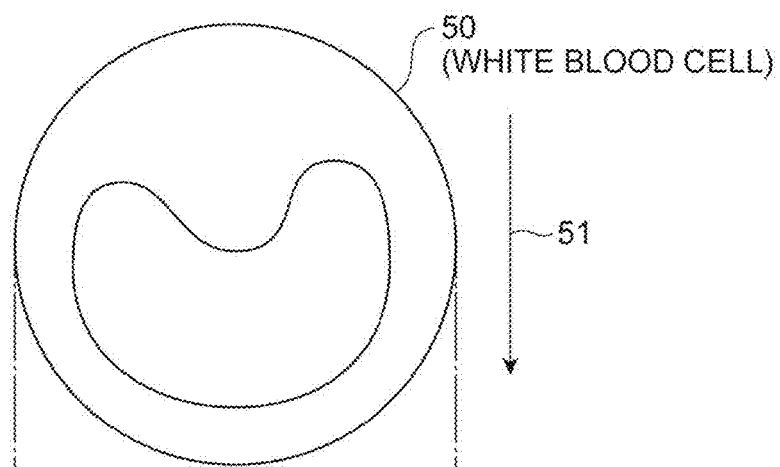
(b)
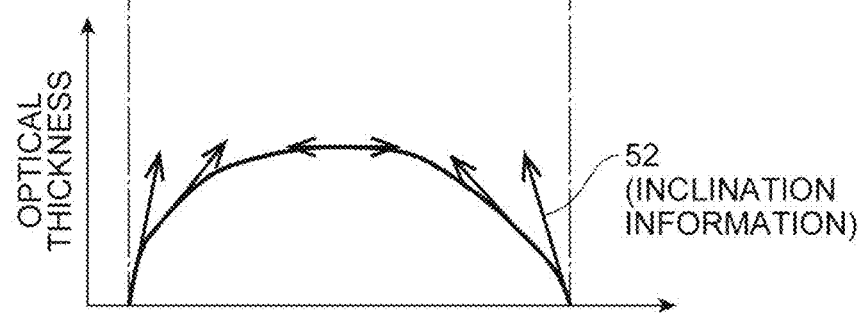

Fig.12
(a)
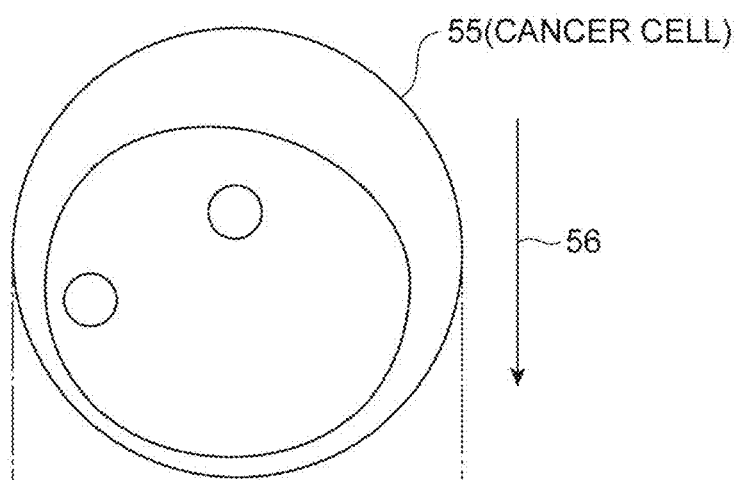
(b)
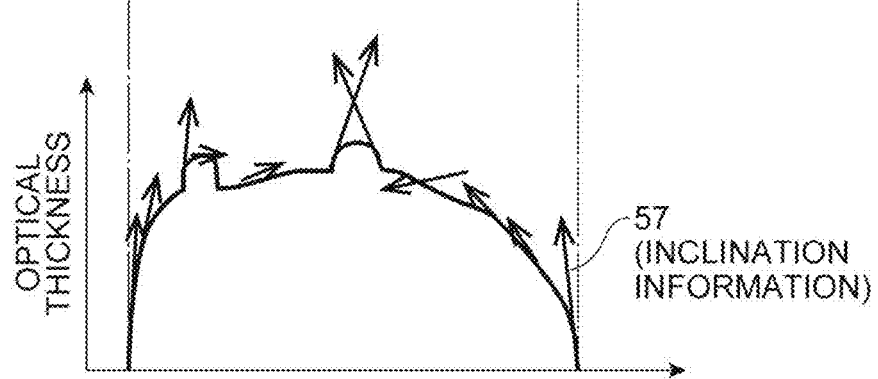

IDENTIFICATION DEVICE AND IDENTIFICATION METHOD

TECHNICAL FIELD

An aspect of the present invention relates to an identification apparatus and an identification method for identifying an object using an image of an optical thickness distribution of the object.

BACKGROUND ART

In general, an object can be identified based on size, shape, or color of the object. However, as in a case of white blood cells and cancer cells for example, when the objects have three-dimensional shapes, have sizes and shapes not significantly different from each other, and are colorless and transparent, the objects cannot be identified in an image obtained with a bright field microscope. Further, although a phase contrast microscope and a differential interference microscope are used for visualizing colorless and transparent cells, these microscopes lack quantitativity for optical thickness. In addition, depending on an objective lens used, these microscopes have a focus depth less than the thickness of a cell, and as a result, only two-dimensional information can be obtained in spite of the fact that the cell has a three-dimensional structure, and the object cannot be identified.

Cells which are released from an original tumor tissue or a metastatic tumor tissue and infiltrate into blood are called circulating tumor cells. The CTCs are present in a trace amount in the peripheral blood of solid cancer patients, are presumed to be associated with metastasis, and have been actively studied in recent years. On the other hand, it is important to identify white blood cells and cancer cells since most all of nucleated cells in the peripheral blood are white blood cells.

It has been reported that in a clinical application of circulating tumor cells, regarding breast cancer patients, when the number of circulating tumor cells in 7.5 mL of whole blood is less than 5, the one-year mortality is 19%, and when the number of circulating tumor cells is 5 or more, the one-year mortality is 53%. Accordingly, it is thought that identification and testing of circulating tumor cells are of great value in clinical applications, for example, are helpful for prognosis expectation.

In the invention disclosed in Patent Document 1, an image of a cell is acquired by an optical system for obtaining a bright field image, feature parameters (such as size, color information, and circularity) of the image are extracted, and the cell is identified based on the feature parameters. In addition, when identifying cells, a pattern recognition process is performed by using a neural network in that invention.

CITATION LIST

Patent Literature

Patent Document 1: Japanese Patent Publication No. 5470625

SUMMARY OF INVENTION

Technical Problem

In the invention disclosed in Patent Document 1, a pattern recognition process is performed for an image of an object acquired by an optical system for obtaining a bright field image, and thereby the object is identified, and therefore, it is difficult to identify objects (phase objects) which have three-dimensional shapes, and have no significant difference therebetween in any of sizes, shapes and colors, as in a case of white blood cells and cancer cells.

An aspect of the present invention has been made in order to solve the above problem, and an object thereof is to provide an apparatus and a method capable of identifying an object even when the object has a three-dimensional shape, has a size and a shape with no distinctive feature, and is colorless and transparent.

Solution to Problem

An identification apparatus according to an aspect of the present invention includes (1) a feature quantity extraction unit for extracting a feature quantity of an image of an optical thickness distribution of an object; (2) a storage unit for storing a result of machine learning performed based on the feature quantity extracted by the feature quantity extraction unit for the image of the optical thickness distribution of an object of which a type is known (hereinafter referred to as a known object); and (3) an identification unit for determining, based on the feature quantity extracted by the feature quantity extraction unit for the image of the optical thickness distribution of an object of which a type is unknown (hereinafter referred to as an unknown object), the type of the unknown object using the learning result stored by the storage unit, and the learning result stored by the storage unit is used when extracting the feature quantity of the image of the optical thickness distribution of the unknown object, or when determining the type of the unknown object, and the feature quantity extraction unit extracts information regarding a spatial change amount of an optical thickness at a position in the image of the optical thickness distribution as the feature quantity of the image.

An identification method according to an aspect of the present invention includes (1) a first feature quantity extraction step of extracting, by a feature quantity extraction unit, a feature quantity of an image of an optical thickness distribution of an object of which a type is unknown (hereinafter referred to as an unknown object); and (2) an identification step of determining the type of the unknown object based on the feature quantity extracted in the first feature quantity extraction step, using a learning result stored by a storage unit obtained by performing machine learning based on a feature quantity extracted by the feature quantity extraction unit for an image of an optical thickness distribution of an object of which a type is known (hereinafter referred to as a known object), and the learning result stored by the storage unit is used when extracting the feature quantity of the image of the optical thickness distribution of the unknown object, or when determining the type of the unknown object, and the feature quantity extraction unit extracts information regarding a spatial change amount of an optical thickness at a position in the image of the optical thickness distribution as the feature quantity of the image.

Advantageous Effects of Invention

According to an aspect of the present invention, even when an object has a three-dimensional shape, has a size and a shape with no distinctive feature, and is colorless and transparent, it is possible to identify the object.

BRIEF DESCRIPTION OF DRAWINGS

FIG. 3 includes (a), (b) views schematically illustrating a structure of a cell.

FIG. 4 includes (a), (b) diagrams illustrating an example of a quantitative phase image of cancer cells.

FIG. 5 includes (a), (b) diagrams illustrating an example of a quantitative phase image of white blood cells.

FIG. 11 includes views schematically illustrating (a) a structure of a white blood cell and (b) inclination information of an optical thickness.

FIG. 12 includes views schematically illustrating (a) a structure of a cancer cell and (b) inclination information of an optical thickness.

DESCRIPTION OF EMBODIMENTS

Hereinafter, an embodiment for carrying out an identification apparatus and an identification method according to an aspect of the present invention will be described in detail with reference to the accompanying drawings. In the description of the drawings, the same reference signs are attached to the same components, and overlapping description will be omitted. In the following, although cells (mainly white blood cells and cancer cells) will be described as an object, the same holds for other objects.

Figure 1:
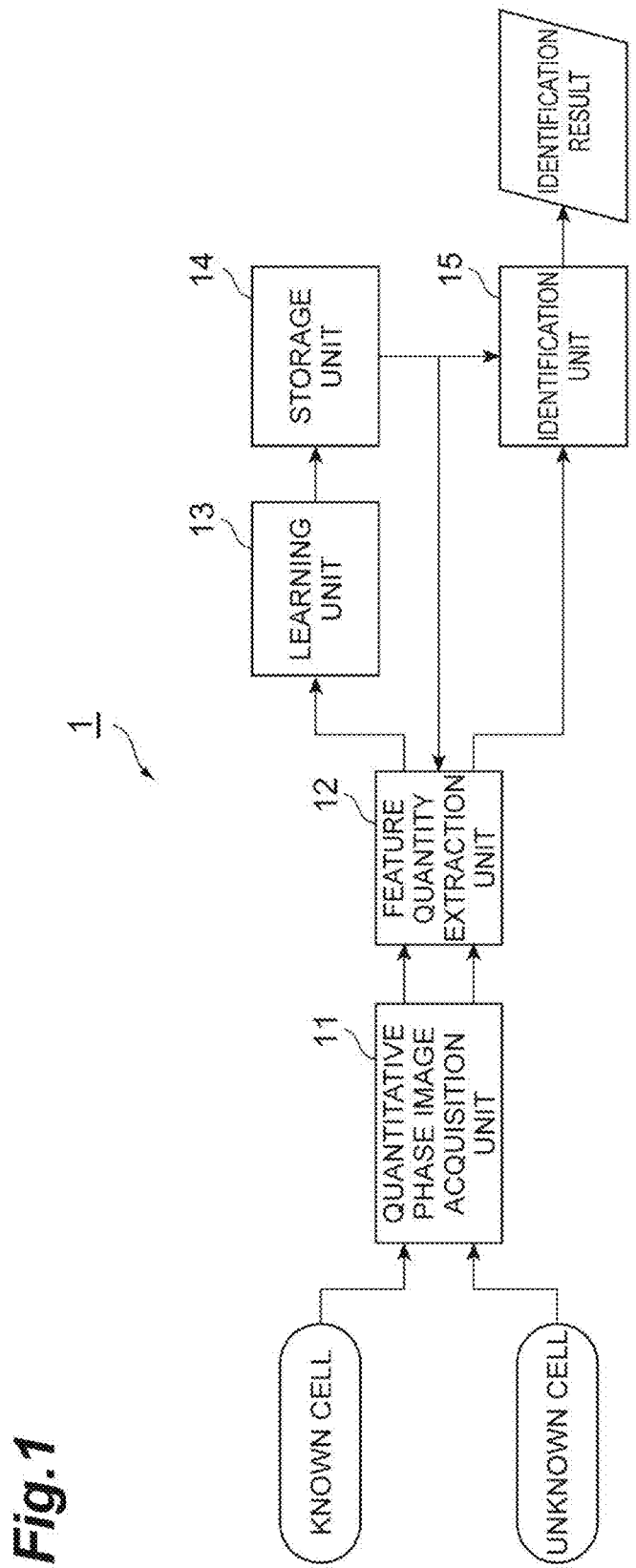
FIG. 1 is a diagram illustrating a configuration of an identification apparatus 1 of an embodiment.

FIG. 1 is a diagram illustrating a configuration of an identification apparatus 1 of an embodiment. The identification apparatus 1 includes a quantitative phase image acquisition unit 11, a feature quantity extraction unit 12, a learning unit 13, a storage unit 14, and an identification unit 15.

The quantitative phase image acquisition unit 11 acquires a quantitative phase image of an object (cell). The quantitative phase image is an image of an optical thickness distribution of the cell. The optical thickness is a product of a physical length along a travelling direction of light and a refractive index. Accordingly, if the physical length of the cell is spatially uniform, the optical thickness distribution of the cell is equivalent to a refractive index distribution. If the refractive index of the cell is spatially uniform, the optical thickness distribution of the cell is equivalent to a physical length distribution. The quantitative phase image may be a one-dimensional image, or may be a two-dimensional image or a three-dimensional image. The three-dimensional quantitative phase image is a special case of the one-dimensional or two-dimensional quantitative phase image, and indicates a three-dimensional spatial distribution of refractive index of the cell. In other words, it indicates information in which the refractive index and the physical length, which characterize the optical thickness, are separated.

The feature quantity extraction unit 12 extracts a feature quantity of the quantitative phase image of the cell acquired by the quantitative phase image acquisition unit 11. The feature quantity extraction unit 12 expresses an individual cell by the quantitative phase image including fixed m×n pixels, performs a smoothing process if necessary, and then extracts the feature quantity of the image. The feature quantity may be, for example, a maximum value of the optical thickness, or information regarding a magnitude of a change in the optical thickness with respect to a position (inclination of the optical thickness). In addition, the feature quantity extraction unit 12 extracts the feature quantity of the quantitative phase image acquired by the quantitative phase image acquisition unit 11 using a learning result stored by the storage unit 14 described later.

The learning unit 13 performs machine learning for a quantitative phase image of a cell of which the type is known (known cell) based on a feature quantity extracted by the feature quantity extraction unit 12. The machine learning is, for example, statistical machine learning, and supervised learning, unsupervised learning, semi-supervised learning, reinforcement learning, transduction, multi-task learning, or deep learning, or the like. For example, in the supervised learning, data of a known cell is employed as training data, data of an unknown cell is employed as test data, a plurality of training data is given to a computer in advance, and a function which performs proper output in response to input test data is generated. The storage unit 14 stores a result of the machine learning (for example, the function obtained by the machine learning) by the learning unit 13. Based on the feature quantity extracted by the feature quantity extraction unit 12 for the quantitative phase image of the cell of which the type is unknown (unknown cell), the identification unit 15 determines the type of the unknown cell using the learning result stored by the storage unit 14.

As the quantitative phase image acquisition unit 11, for example, a quantitative phase microscope is used. As the feature quantity extraction unit 12, the learning unit 13, the storage unit 14, and the identification unit 15, for example, a computer including a processor and a memory is used. In this case, the computer executes functions as the feature quantity extraction unit 12, the learning unit 13, and the identification unit 15, by the processor. In addition, the computer executes a function of the storage unit 14 by the memory or an external storage device. Accordingly, the computer includes the feature quantity extraction unit 12, the learning unit 13, the storage unit 14, and the identification unit 15. As a feature quantity extraction algorithm, for example, HOG (histograms of oriented gradients), LBP (local binary pattern), GLAC (gradient local auto-correlation), HLAC (higher-order local auto-correlation), and Haar-like, and the like are used. As a machine learning algorithm, for example, AdaBoost (adaptive boosting), Mahalanobis K-means, naive Bayes classifier, decision tree, boosting, random trees, expectation maximization, K-nearest neighbors, neural network, multi-layer perceptron (MPL), support vector machine, and deep learning, and the like are used.

Figure 2:
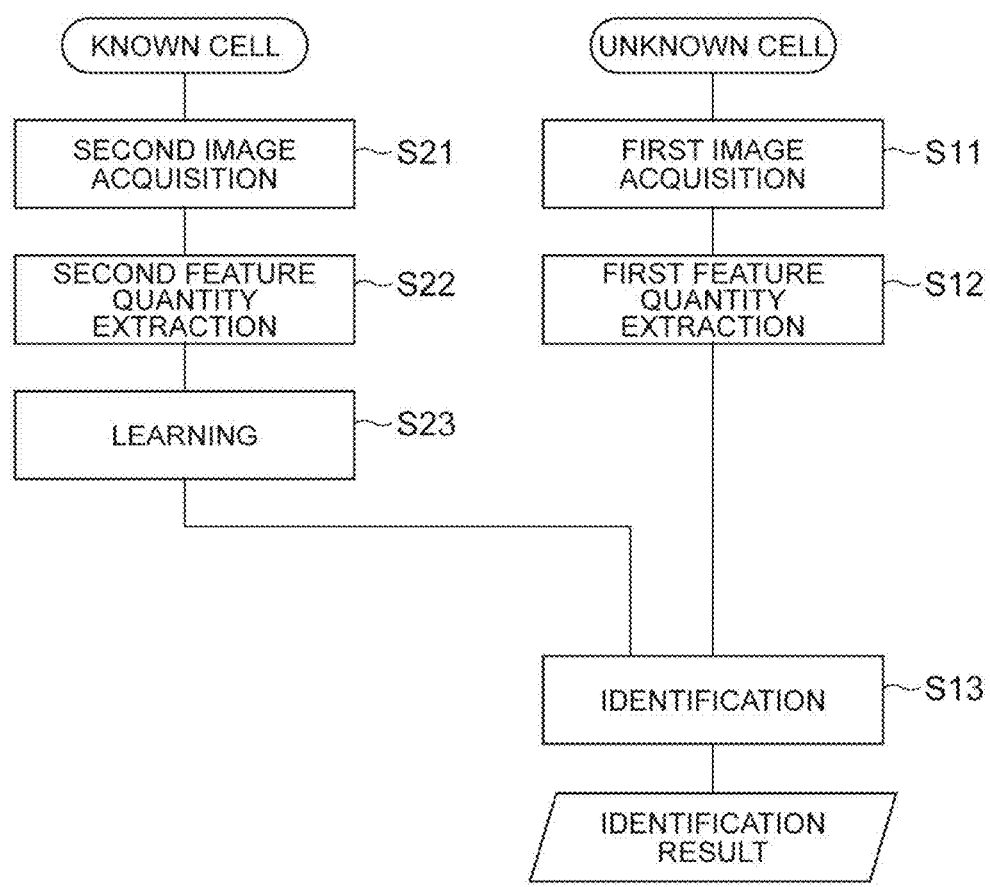
FIG. 2 is a flowchart for explaining an identification method of the embodiment.

Next, an operation of the identification apparatus 1 of the embodiment will be described, as well as the identification method of the embodiment will be described. FIG. 2 is a flowchart for explaining the identification method of the embodiment. The identification method of the embodiment includes a first image acquisition step S11, a first feature quantity extraction step S12, an identification step S13, a second image acquisition step S21, a second feature quantity extraction step S22, and a learning step S23.

In the second image acquisition step S21, a quantitative phase image of many known cells is acquired by the quantitative phase image acquisition unit 11. In the subsequent second feature quantity extraction step S22, a feature quantity of the quantitative phase image of these known cells is extracted by the feature quantity extraction unit 12. Then, in the learning step S23, machine learning is performed in the learning unit 13 based on the feature quantity extracted in the second feature quantity extraction step S22, and a learning result thereof is stored in the storage unit 14. In a case where white blood cells are identified in the identification step S13, as for the many known cells, it is preferable to acquire quantitative phase images of white blood cells and cells other than white blood cells by the quantitative phase image acquisition unit 11. In addition, in a case where cancer cells are identified in the identification step S13, as for the many known cells, it is preferable to acquire quantitative phase images of cancer cells and cells other than cancer cells by the quantitative phase image acquisition unit 11.

Here, the white blood cells may be those collected from a cancer patient, or may be those collected from a healthy person. The white blood cells may be those to which a hemolytic agent is added. The cancer cells may be collected circulating tumor cells, or may be cultured cancer cells.

In the first image acquisition step S11, a quantitative phase image of an unknown cell is acquired by the quantitative phase image acquisition unit 11. In the subsequent first feature quantity extraction step S12, a feature quantity of the quantitative phase image of the unknown cell is extracted by the feature quantity extraction unit 12. Then in the identification step S13, the type of the unknown cell is determined in the identification unit 15 based on the feature quantity extracted in the first feature quantity extraction step S12 using the learning result stored by the storage unit 14.

Next, a structure of a cell will be described, as well as a quantitative phase image of a cell and a feature quantity will be described. FIG. 3 includes views schematically illustrating the structure of the cell. In FIG. 3, an xyz orthogonal coordinate system is illustrated for the convenience of description. The cell 30 is placed on a preparation 40 disposed in parallel to an xy plane. (a) in FIG. 3 illustrates a sectional view of the cell 30 in parallel to an xz plane. (b) in FIG. 3 illustrates a plan view of the cell 30 viewing in a direction of an optical axis in parallel to a z-axis. The cell 30 has a structure in which a cell nucleus 31 present in a central region is covered with cytoplasm 32, and the cytoplasm 32 is enveloped by a cell membrane 33.

As illustrated in FIG. 3, common cells have a structure including a cell nucleus, cytoplasm, and a cell membrane. The shapes and the refractive indices of the cell nuclei, the cytoplasm and the cell membranes vary depending on the type of cell such as a white blood cell or a cancer cell. In addition, it is known that the size and shape of a cell nucleus are changed in general when a normal cell turns into a cancer cell. However, since a definite shape of cancer cells in the blood is unknown, the following description will be given for not the cancer cells in the blood, but for common cancer cells.

When the quantitative phase image acquisition unit 11 is used and light is transmitted through a cell in an optical axis direction (z direction), phase delay of the light varies depending on positions on the xy plane in accordance with the refractive index and the shape of each of a cell nucleus, cytoplasm, and a cell membrane. A quantitative phase image acquired by the quantitative phase image acquisition unit 11 indicates the phase delay distribution, and indicates the optical thickness distribution of the cell. Each of pixel values of the quantitative phase image corresponds to the optical thickness at an xy position corresponding to the pixel. As described above, the quantitative phase image is in accordance with the refractive index and the shape of each of the cell nucleus, the cytoplasm, and the cell membrane. Therefore, the type of the cell can be determined based on the quantitative phase image of the cell.

FIG. 4 includes diagrams illustrating an example of a quantitative phase image of cancer cells (HepG2). FIG. 5 includes diagrams illustrating an example of a quantitative phase image of white blood cells. (a) in FIG. 4 and (a) in FIG. 5 illustrate each a quantitative phase image. (b) in FIG. 4 and (b) in FIG. 5 illustrate each an optical thickness distribution of the cell along a dashed line illustrated in (a) in the corresponding figure. As it can be seen from comparison between the respective quantitative phase images of the cancer cells and the white blood cells, there are differences between them in terms of maximum values of the optical thickness, and the inclination of the optical thickness. Accordingly, these may be extracted as the feature quantity of the quantitative phase images by the feature quantity extraction unit 12.

Next, the inclination of the optical thickness will be further described. In the embodiment, it is preferable to identify a white blood cell and a cancer cell by extracting inclination information of an optical thickness as a feature quantity of a quantitative phase image by the feature quantity extraction unit 12, and performing image recognition based on the inclination information. The inclination information is information regarding inclination of a graph obtained when a horizontal axis represents a position and a vertical axis represents an optical thickness, as illustrated in (b) in FIG. 4 and (b) in FIG. 5, a vector in the xy plane, or the like. The inclination information does not indicate inclination of a surface of the cell, but reflects a structure in the cell such as the shape and the refractive index of a cell nucleus and the like constituting the cell.

When inclination information is extracted in the feature quantity extraction unit 12 as a feature quantity of a quantitative phase image of a cell using the HOG as a feature quantity extraction algorithm, for example, the following feature quantity extraction process is performed. A pixel value I(x, y) of a pixel located at a position (x, y) in the quantitative phase image corresponds to the optical thickness. For the pixel located at the position (x, y) in the quantitative phase image, a difference fx(x, y) between pixel values I(x+1, y) and I(x−1, y) of two vicinal pixels in an x-direction is obtained by the following formula (1), and a difference fy(x, y) between pixel values I(x, y+1) and I(x, y−1) of two vicinal pixels in a y-direction is obtained by the following formula (2).

[Formula 1]
$$f_x(x,y)=I(x+1,y)-I(x-1,y) \quad (1)$$

[Formula 2]
$$f_y(x,y)=I(x,y+1)-I(x,y-1) \quad (2)$$

A magnitude (gradient magnitude) of a vector (fx(x, y), fy(x, y)) in the xy plane is represented by m(x, y) obtained by the following formula (3). In addition, inclination (gradient direction) of the vector (fx(x, y), fy(x, y)) in the xy plane is represented by θ(x, y) obtained by the following formula (4).

[Formula 3]

$$m(x, y) = \sqrt{f_x^2 + f_y^2} \quad (3)$$

[Formula 4]

$$\theta(x, y) = \arctan\frac{f_y}{f_x} \quad (4)$$

Figure 6:
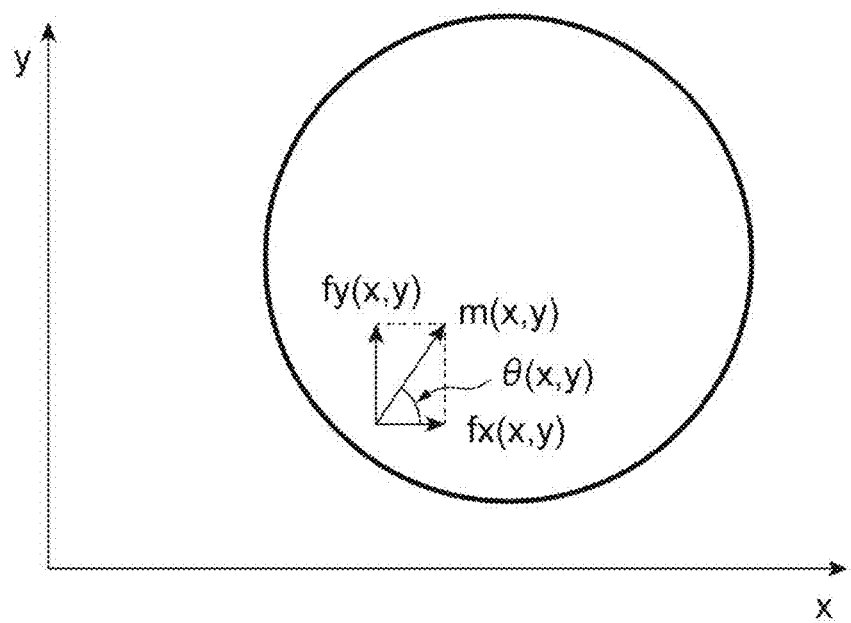
FIG. 6 is a drawing for explaining fx(x, y), fy(x, y), m(x, y) and θ(x, y) in a quantitative phase image.

FIG. 6 is a drawing for explaining fx(x, y), fy(x, y), m(x, y), and θ(x, y) in the quantitative phase image. In FIG. 6, a region of a cell in the quantitative phase image is represented as substantially a circular shape, and a relationship among fx(x, y), fy(x, y), m(x, y), and θ(x, y) at a certain point in the region is explained.

Figure 7:
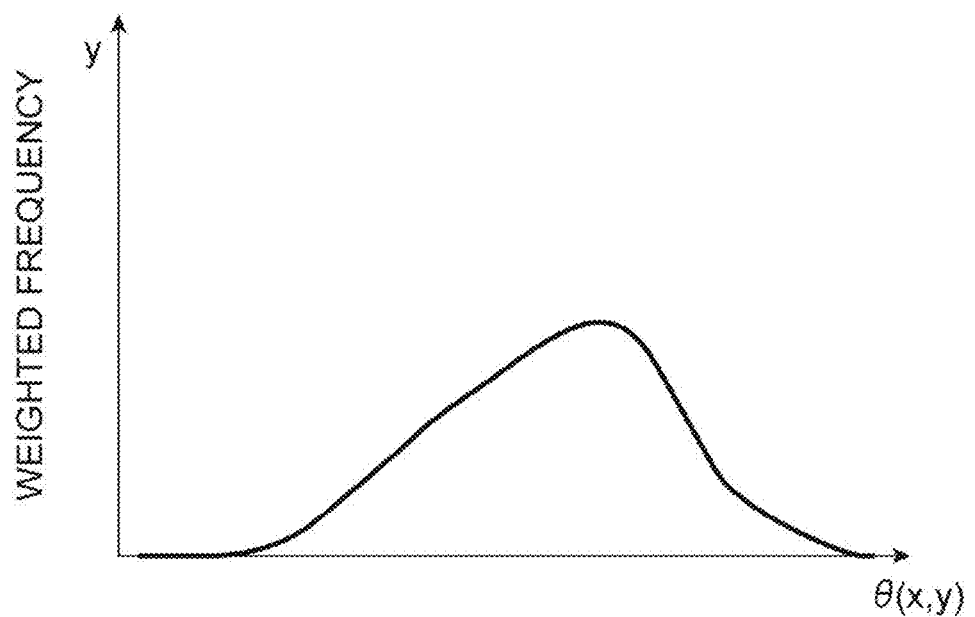
FIG. 7 is a drawing illustrating an example of a histogram of a gradient direction θ(x, y) obtained by weighing with a gradient magnitude m(x, y).

The gradient magnitude m(x, y) and the gradient direction θ(x, y) are obtained for all pixels in the quantitative phase image and a histogram of the gradient direction θ(x, y) is obtained. At this time, weighing is performed with the gradient magnitude m(x, y). FIG. 7 is a drawing illustrating an example of the histogram of the gradient direction θ(x, y) obtained by weighing with the gradient magnitude m(x, y). The shape of the histogram varies depending on the type of cell. Accordingly, it is possible to identify cancer cells and white blood cells based on the shape of the histogram.

Figure 10:
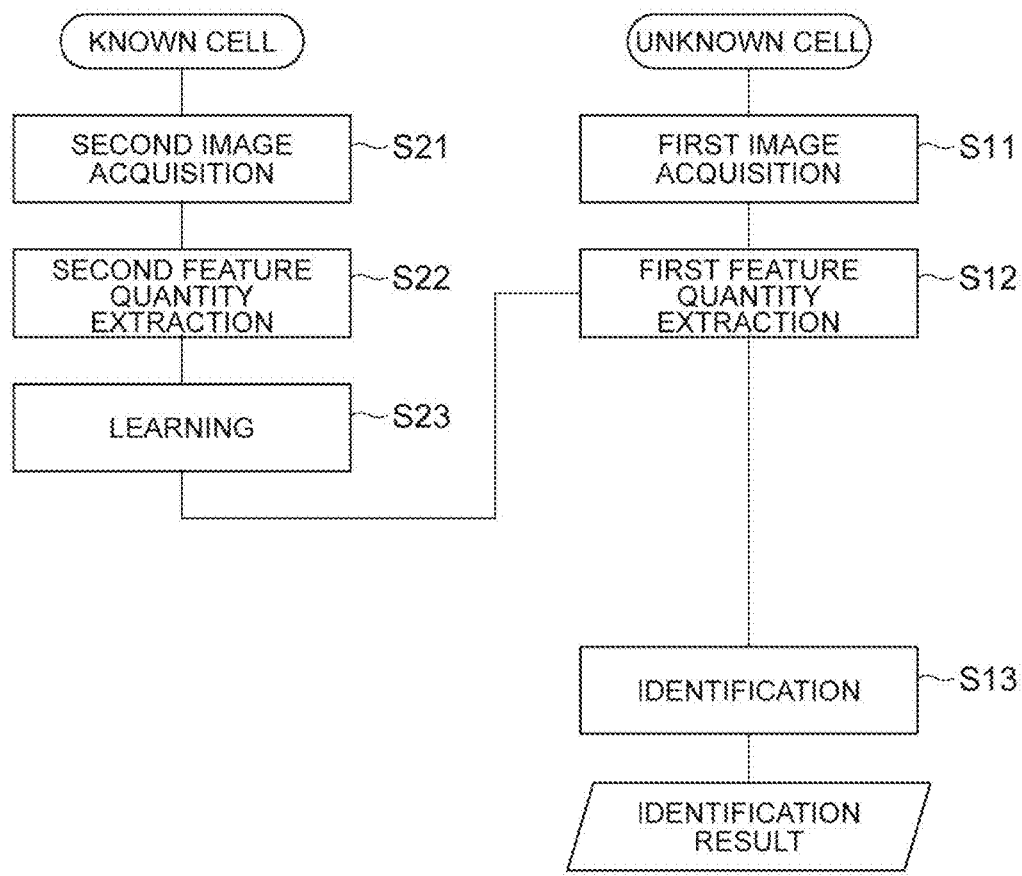
FIG. 10 is a flowchart for explaining another example of the identification method of the embodiment.

As illustrated in FIG. 10, using a result of machine learning with a known cell, a feature quantity of an unknown cell can be extracted by the feature quantity extraction unit 12 in the first feature quantity extraction step S12. It takes time to extract a feature quantity for all pixels in a quantitative phase image of the unknown cell, and therefore, among all pixels in the quantitative phase image, one or more regions are set as a region (a position or a pixel) from which a feature quantity is extracted based on the result of machine learning with the known cell, and accordingly, it is possible to substantially reduce time taken to determine the cell. A range of the set region may be that including at least one pixel which constitutes the quantitative phase image.

Next, an example will be described in which white blood cells were identified, from a cell population including cancer cells and white blood cells mixed with each other, by extracting the feature quantity as described above. In the example, 240 white blood cells collected from a healthy person were used as known cells (positive cells) and 71 cultured cancer cells were used as known cells (negative cells), and the second image acquisition step S21, the second feature quantity extraction step S22, and the learning step S23 were performed. The details of the 71 cultured cancer cells are as follows; the number of cells of cell line HCT116, cell line DLD1, cell line HepG2, and cell line Panel are 18, 21, 7, and 25, respectively. As the white blood cells, those to which a hemolytic agent had been added and those to which no hemolytic agent had been added were used.

The quantitative phase image of each cell, which was originally about 150×150 pixels in size, was converted into an 8-bit black-and-white image, and reduced to an image of 24×24 pixels, 48×48 pixels, or 72×72 pixels in size, and feature quantity extraction and machine learning were performed using the reduced images. HOG and AdaBoost included in OpenCV (Version 2.4.8) were used as the algorithm. The machine learning at each stage was stopped at a misdiagnosis rate of 0.4.

Figure 8:
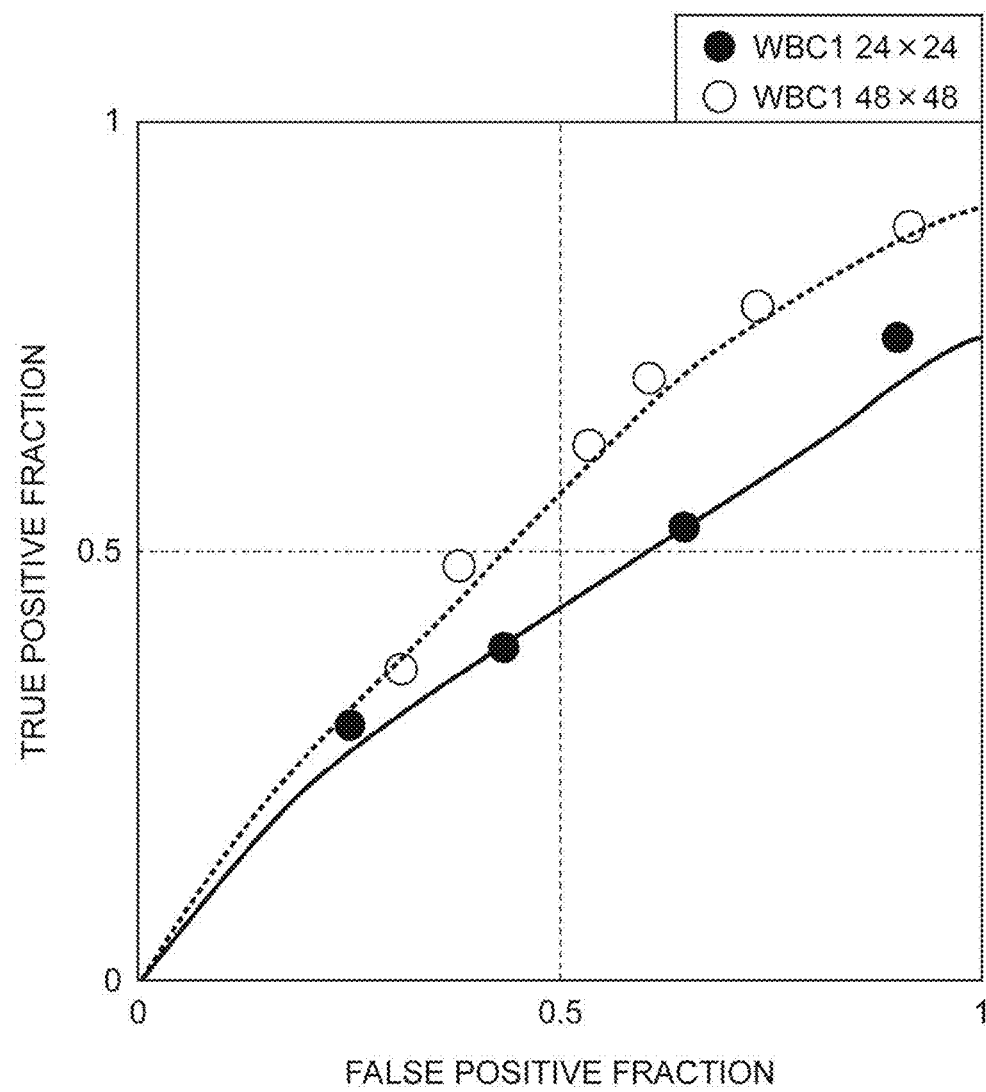
FIG. 8 is a view illustrating ROC curves obtained when machine learning is performed using white blood cells to which no hemolytic agent is added.

FIG. 8 is a view illustrating ROC curves obtained when the machine learning is performed using white blood cells to which no hemolytic agent is added. In FIG. 8, "WBC1" means that the machine learning was performed using white blood cells to which no hemolytic agent had been added. Among three ROC curves in FIG. 8, the ROC curve of "WBC1 24×24" is a curve obtained when the size of a white blood cell image was reduced to 24×24 pixels. In addition, the ROC curve of "WBC1 48×48" is a curve obtained when the size of the white blood cell image was reduced to 48×48 pixels.

Figure 9:
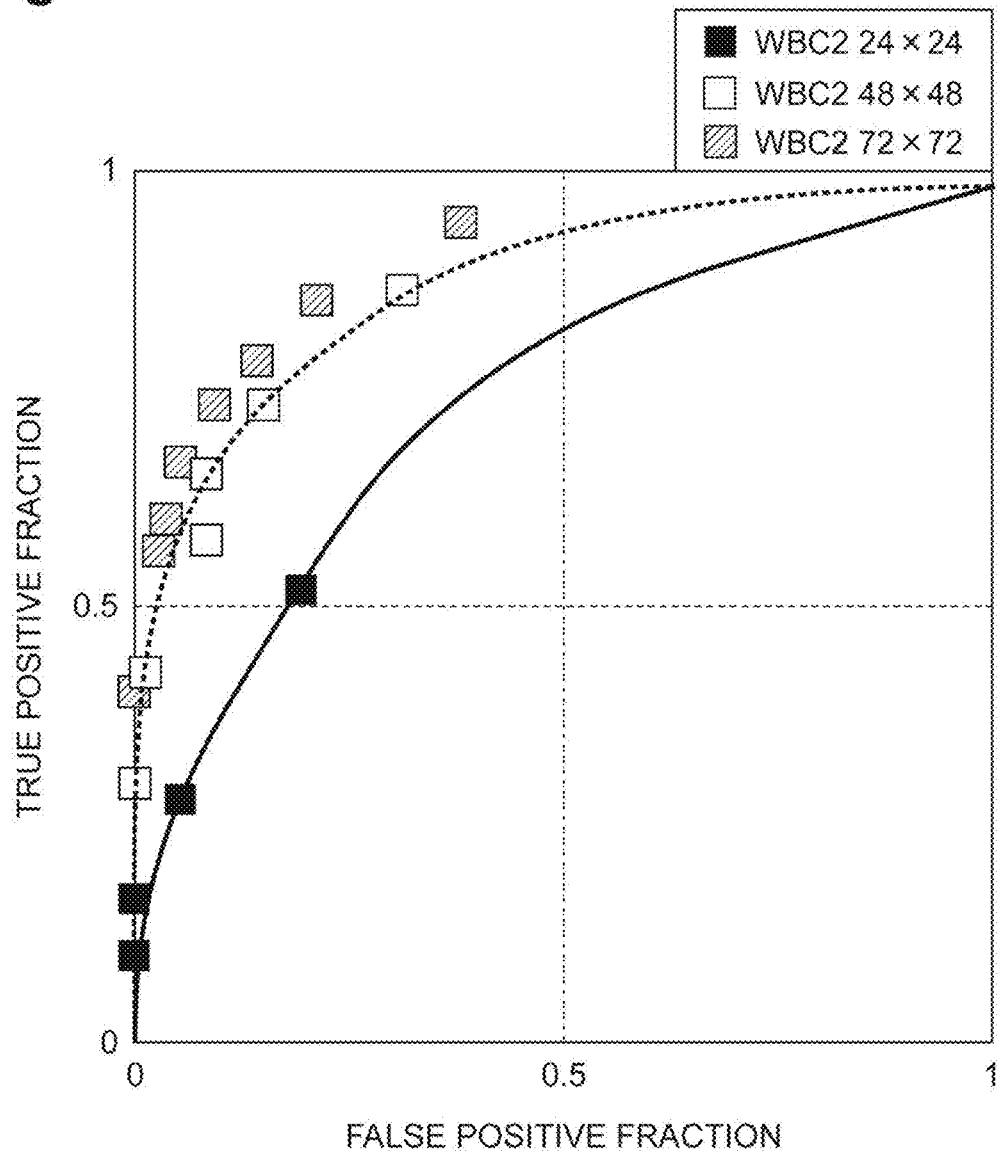
FIG. 9 is a view illustrating ROC curves obtained when machine learning is performed using white blood cells to which a hemolytic agent is added.

FIG. 9 is a view illustrating ROC curves obtained when the machine learning is performed using white blood cells to which a hemolytic agent is added. In FIG. 9, "WBC2" means that the machine learning was performed using white blood cells to which a hemolytic agent had been added. Among three ROC curves in FIG. 9, the ROC curve of "WBC2 24×24" is a curve obtained when the size of a white blood cell image was reduced to 24×24 pixels. In addition, the ROC curve of "WBC2 48×48" is a curve obtained when the size of the white blood cell image was reduced to 48×48 pixels. In addition, the ROC curve of "WBC2 72×72" is a curve obtained when the size of the white blood cell image was reduced to 72×72 pixels.

The ROC (receiver operating characteristic) curves indicate performance of identification by the identification unit 15 using the result of the machine learning by the learning unit 13. The horizontal axis represents a false positive fraction which indicates a probability that an object, which is not actually a white blood cell, is erroneously determined to be a white blood cell. The vertical axis represents a true positive fraction which indicates a probability that an object, which is actually a white blood cell, is properly determined to be a white blood cell. The closer an ROC curve is present to a left upper corner, the higher the accuracy of identification. An AUC (area under the curve) is an area of a region under the ROC curve. What is meant by that the AUC is large (in other words, the AUC is close to a value 1) is that the ROC curve is present close to the left upper corner, which indicates that the accuracy of identification is high.

As it can be seen from FIG. 8 and FIG. 9, the more the number of pixels of cell images, the larger the AUC. In addition, a larger AUC is obtained when the machine learning is preformed using white blood cells to which a hemolytic agent is added. Similar ROC curves were obtained also in a case where a combination of cell lines of cancer cells different from that described above was used for the machine learning. Therefore, in order to identify cancer cells and white blood cells with high accuracy, the number of pixels of a cell image is preferably large (for example, 48×48 or more), and machine learning is preferably performed using white blood cells to which a hemolytic agent is added.

Such machine learning is performed and a learning result thereof is stored in the storage unit 14. When performing identification of an unknown cell or extraction of a feature quantity thereafter, the identification or the extraction of the feature quantity may be performed using the learning result stored in the storage unit 14, and therefore, there is no need to use the learning unit 13, and to perform the second image acquisition step S21, the second feature quantity extraction step S22, and the learning step S23.

In addition, an example will be illustrated in which inclination information is extracted by the feature quantity extraction unit 12 as a feature quantity of a quantitative phase image (image of optical thickness distribution) of a cell, and discrimination between white blood cells and cancer cells is performed. Here, FIG. 11 includes views schematically illustrating (a) a structure of a white blood cell and (b) inclination information of an optical thickness. In (a)

in FIG. 11, an arrow 51 indicates a direction of the optical thickness in the white blood cell 50. In (b) in FIG. 11, an arrow 52 indicates inclination information in optical thickness distribution. In addition, FIG. 12 includes views schematically illustrating (a) a structure of a cancer cell and (b) inclination information of an optical thickness. In (a) in FIG. 12, an arrow 56 indicates a direction of the optical thickness in the cancer cell 55. In (b) in FIG. 12, an arrow 57 indicates inclination information in optical thickness distribution.

Figure 13:
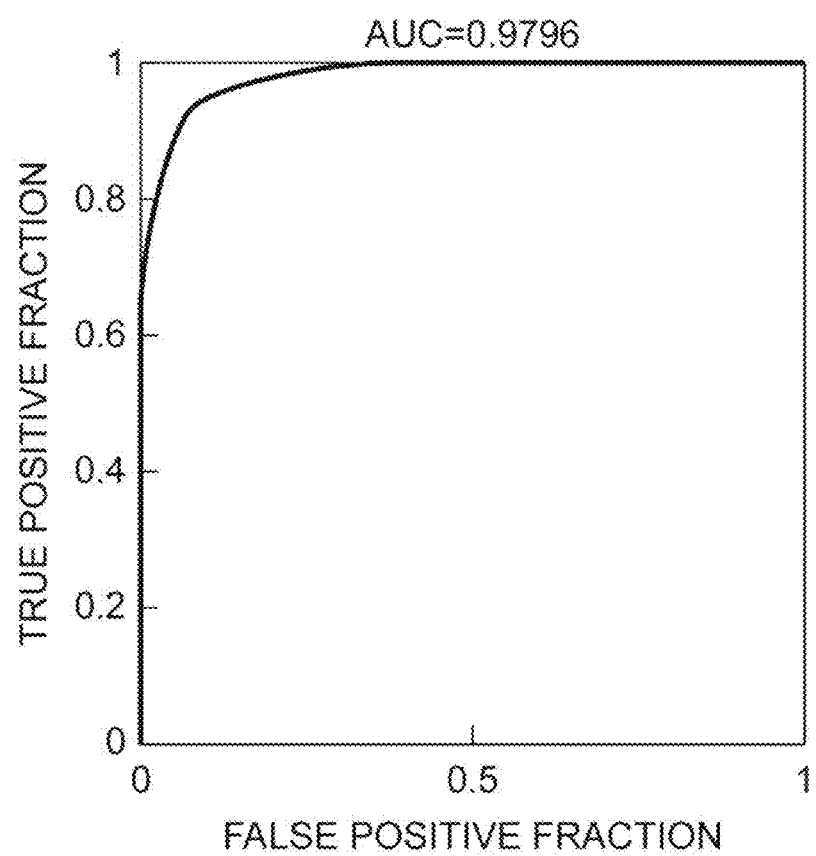
FIG. 13 is an ROC curve illustrating a relationship between a false positive fraction and a true positive fraction of white blood cells when performing discrimination between white blood cells and cancer cells.

FIG. 13 is an ROC curve illustrating a relationship between a false positive fraction and a true positive fraction of white blood cells at discrimination between white blood cells and cancer cells using inclination information extracted as a feature quantity of a quantitative phase image. Here, as a feature quantity extraction algorithm, HOG is used. As it can be seen from FIG. 13, in the example, the AUC value is as very high as about 0.98, which indicates that it is possible to determine the cancer cell and the white blood cell with high accuracy.

The identification apparatus and the identification method according to an aspect of the present invention are not limited to the embodiment and the configuration examples described above, and may be modified in various ways.

The identification apparatus according to the above embodiment has a configuration which includes (1) a feature quantity extraction unit for extracting a feature quantity of an image of an optical thickness distribution of an object; (2) a storage unit for storing a learning result of machine learning performed based on the feature quantity extracted by the feature quantity extraction unit for the image of the optical thickness distribution of an object of which a type is known (a known object); and (3) an identification unit for determining, based on the feature quantity extracted by the feature quantity extraction unit for the image of the optical thickness distribution of an object of which a type is unknown (an unknown object), the type of the unknown object using the learning result stored by the storage unit, and the learning result stored by the storage unit is used when extracting the feature quantity of the image of the optical thickness distribution of the unknown object, or when determining the type of the unknown object.

The identification apparatus having the above configuration preferably further includes (4) a learning unit for performing machine learning based on the feature quantity extracted by the feature quantity extraction unit for the image of the optical thickness distribution of the known object, and (5) the storage unit preferably stores the learning result of machine learning by the learning unit.

The identification method according to the above embodiment has a configuration which includes (1) a first feature quantity extraction step of extracting, by a feature quantity extraction unit, a feature quantity of an image of an optical thickness distribution of an object of which a type is unknown (an unknown object); and (2) an identification step of determining the type of the unknown object based on the feature quantity extracted in the first feature quantity extraction step, using a learning result stored by a storage unit obtained by performing machine learning based on a feature quantity extracted by the feature quantity extraction unit for an image of an optical thickness distribution of an object of which a type is known (a known object), and the learning result stored by the storage unit is used when extracting the feature quantity of the image of the optical thickness distribution of the unknown object, or when determining the type of the unknown object.

The identification method having the above configuration preferably further includes (3) a second feature quantity extraction step of extracting, by the feature quantity extraction unit, the feature quantity of the image of the optical thickness distribution of the known object, and (4) a learning step of performing machine learning based on the feature quantity extracted in the second feature quantity extraction step and causing the storage unit to store the learning result thereof.

In the above configuration, a configuration may be employed in which the feature quantity extraction unit sets at least one region, from which the feature quantity is extracted, in the image of the optical thickness distribution of the unknown object using the learning result stored by the storage unit. Specifically, the identification apparatus may have a configuration in which the feature quantity extraction unit sets at least one region, from which the feature quantity is extracted, in the image of the optical thickness distribution of the unknown object using the learning result stored by the storage unit. Further, the identification method may have a configuration in which, in the first feature quantity extraction step, at least one region, from which the feature quantity is extracted, is set in the image of the optical thickness distribution of the unknown object using the learning result stored by the storage unit.

Further, in the above configuration, a configuration may be employed in which information regarding a spatial change amount of an optical thickness at a position in the image of the optical thickness distribution is extracted as the feature quantity of the image. Specifically, the identification apparatus may have a configuration in which the feature quantity extraction unit extracts information regarding a spatial change amount of an optical thickness at a position in the image of the optical thickness distribution as the feature quantity of the image. Further, the identification method may have a configuration in which the feature quantity extraction unit extracts information regarding a spatial change amount of an optical thickness at a position in the image of the optical thickness distribution as the feature quantity of the image.

A configuration may be employed in which, in particular, the information regarding the spatial change amount of the optical thickness at a position in the image of the optical thickness distribution is one or both of a gradient magnitude and a gradient direction of a vector at the position (pixel) in the image of the optical thickness distribution.

Further, a configuration may be employed in which a white blood cell and a cancer cell are included as the object. Further, a configuration may be employed in which the feature quantity extraction unit extracts the feature quantity of the image of the optical thickness distribution of the object to which a hemolytic agent is added.

In addition, the identification apparatus according to an aspect of the present invention includes a feature quantity extraction unit for extracting a feature quantity of an image of an optical thickness distribution of an object, and an identification unit for determining the type of the object based on the extracted feature quantity, and the feature quantity extraction unit extracts information regarding a spatial change amount of an optical thickness at a position in the image of the optical thickness distribution as the feature quantity of the image.

In addition, the identification method according to an aspect of the present invention includes an extraction step of extracting a feature quantity of an image of an optical thickness distribution of an object, and an identification step of determining the type of the object based on the extracted feature quantity, and in the extraction step, information regarding a spatial change amount of an optical thickness at a position in the image of the optical thickness distribution is extracted as the feature quantity of the image.

As it can be seen from FIG. 13, by performing extraction, for an image of an optical thickness distribution of an object, of information regarding a spatial change amount of an optical thickness at a position in the image of the optical thickness distribution as a feature quantity of the image, it is possible to determine the type of the object with high accuracy.

INDUSTRIAL APPLICABILITY

An aspect of the present invention can be used as an identification apparatus and an identification method capable of identifying an object, even when the object has a three-dimensional shape, has a size and a shape with no distinctive feature, and is colorless and transparent.

REFERENCE SIGNS LIST

1—identification apparatus, 11—quantitative phase image acquisition unit, 12—feature quantity extraction unit, 13—learning unit, 14—storage unit, 15—identification unit.

The invention claimed is:

1. An identification apparatus comprising:
non-transitory computer readable memory;
one or more hardware processors coupled to the non-transitory memory and configured to read instructions from the non-transitory memory to cause the content management apparatus to perform operations comprising:
extracting a feature quantity of an image of an optical thickness distribution of an object;
storing a learning result of machine learning performed based on the feature quantity extracted for the image of the optical thickness distribution of a known object of which a type is known; and
determining, based on the feature quantity extracted for the image of the optical thickness distribution of an unknown object of which a type is unknown, the type of the unknown object using the learning result stored, wherein
the learning result stored is used when extracting the feature quantity of the image of the optical thickness distribution of the unknown object, or when determining the type of the unknown object, and
the operations further comprising extracting information regarding a spatial change amount of an optical thickness at a position in the image of the optical thickness distribution as the feature quantity of the image,
whereby even when an object has a three-dimensional shape, has a size and a shape with no distinctive feature, and is colorless and transparent, it is possible to identify the object.

2. The identification apparatus according to claim 1, the operations further comprising performing the machine learning based on the feature quantity extracted for the image of the optical thickness distribution of the known object, wherein
the learning result of the machine learning is stored.

3. The identification apparatus according to claim 1, wherein at least one region is set, from which the feature quantity is extracted, in the image of the optical thickness distribution of the unknown object using the learning result stored.

4. The identification apparatus according to claim 1, wherein the information regarding the spatial change amount of the optical thickness is one or both of a gradient magnitude and a gradient direction of a vector at the position in the image of the optical thickness distribution.

5. An identification method comprising:
providing one or more hardware processors configured to read instructions from a non-transitory memory to cause the content management apparatus to perform operations comprising:
extracting a feature quantity of an image of an optical thickness distribution of an unknown object of which a type is unknown; and
determining the type of the unknown object based on the feature quantity extracted in the first feature quantity extraction step, using a stored learning result obtained by performing machine learning based on a feature quantity extracted for an image of an optical thickness distribution of a known object of which a type is known, wherein
the learning result stored is used when extracting the feature quantity of the image of the optical thickness distribution of the unknown object, or when determining the type of the unknown object, and
the operations further comprising extracting information regarding a spatial change amount of an optical thickness at a position in the image of the optical thickness distribution as the feature quantity of the image,
whereby even when an object has a three-dimensional shape, has a size and a shape with no distinctive feature, and is colorless and transparent, it is possible to identify the object.

6. The identification method according to claim 5, the operations further comprising:
a second feature quantity extraction step of extracting the feature quantity of the image of the optical thickness distribution of the known object, and
a learning step of performing the machine learning based on the feature quantity extracted in the second feature quantity extraction step and causing the learning result to be stored.

7. The identification method according to claim 5, wherein in the first feature quantity extraction step, at least one region, from which the feature quantity is extracted, is set in the image of the optical thickness distribution of the unknown object using the learning result stored.

8. The identification method according to claim 5, wherein the information regarding the spatial change amount of the optical thickness is one or both of a gradient magnitude and a gradient direction of a vector at the position in the image of the optical thickness distribution.

9. The identification method according to claim 5, wherein a white blood cell and a cancer cell are included as the object.

10. The identification method according to claim 9, wherein the operations further comprise extracting the feature quantity of the image of the optical thickness distribution of the object to which a hemolytic agent is added.

* * * * *